(12) United States Patent
Yoon et al.

(10) Patent No.: US 8,066,990 B2
(45) Date of Patent: Nov. 29, 2011

(54) LYSIN PROTEIN HAVING BROAD ANTIBACTERIAL ACTIVITY SPECIFIC TO BACTERIA

(75) Inventors: Seongjun Yoon, Seoul (KR); Yunjaie Choi, Seoul (KR); Jeesoo Son, Seoul (KR); Sooyoun Jun, Seoul (KR); Hyoungrok Paik, Kwangyang-si (KR); Sanghyeon Kang, Seoul (KR)

(73) Assignee: Intron Biotechnology, Inc., Sungnam-Si, Kyungki-Do (KR)

( * ) Notice: Subject to any disclaimer, the term of this patent is extended or adjusted under 35 U.S.C. 154(b) by 191 days.

(21) Appl. No.: 12/423,322

(22) Filed: Apr. 14, 2009

(65) Prior Publication Data

US 2010/0172918 A1 Jul. 8, 2010

(30) Foreign Application Priority Data

Jan. 8, 2009 (KR) ........................ 10-2009-0001579

(51) Int. Cl.
*A61K 38/46* (2006.01)
(52) U.S. Cl. ........................................ 424/94.6
(58) Field of Classification Search .................. None
See application file for complete search history.

(56) References Cited

U.S. PATENT DOCUMENTS

2009/0304638 A1* 12/2009 Yoon et al. .................. 424/93.6

OTHER PUBLICATIONS

Yoong et al. (J. Bacteriol., 186:4808-4812, 2004).*
Fischetti (Int. J. Med. Microbiol., 300:357-362, 2010).*
Son et al. (J. Appl. Microbiol., 108:1769-1779, 2010).*
Borysowski, J.; Weber-Darbrowska, B., and Gárski, A. "Bacteriophage Endolysins as a Novel Class of Antibacterial Agents." *Exp. Biol. Med.* 231:366-377 (2006).

* cited by examiner

*Primary Examiner* — Nita M Minnifield
*Assistant Examiner* — Brian J Gangle
(74) *Attorney, Agent, or Firm* — Ballard Spahr LLP

(57) ABSTRACT

The present invention relates to a lysin protein originated from bacteriophage, more precisely a lysin protein comprising the amino acid sequence represented by SEQ. ID. NO: 2 which has no harm to human and animals comprising eukaryotic cells owing to its specificity to bacteria and has broad antibacterial activity, and a pharmaceutical composition for the prevention and treatment of infectious disease caused by bacteria comprising the said lysin protein as an active ingredient.

12 Claims, 2 Drawing Sheets

Salmonella enteritidis

Lactococcus lactis

LYSIN PROTEIN HAVING BROAD ANTIBACTERIAL ACTIVITY SPECIFIC TO BACTERIA

CROSS REFERENCE TO RELATED APPLICATIONS

This application claims priority to Korean Patent Application No. 2009/0001579, filed Jan. 8, 2009, which application is incorporated by this reference in its entirety.

TECHNICAL FIELD

The present invention relates to a bacteriophage-originated novel lysin protein having broad antibacterial activity specific to bacteria, which is distinguished from the reported lysin protein in specificity to bacteria, and a pharmaceutical composition for the prevention and treatment of infectious disease caused by bacteria comprising the said lysin protein as an active ingredient.

BACKGROUND ART

Infectious organisms, particularly bacteria, are threatening almost every living thing including human, animals and plants. According to rapid global warming, new infectious organisms would emerge and thereby infectious diseases are increasing consistently. Threat by such infectious organisms is more serious than intractable disease such as cancer, diabetes mellitus, stroke and leukemia.

Antibiotics have been regarded as the drugs closely related to human health for almost 100 years. The first antibiotic to treat infectious disease caused by bacteria was penicillin isolated from *Penicillium notatum* by Alexander Fleming in 1920s. Since then, diverse antibiotics have been developed based on the structure of penicillin, which seems to free human from infectious bacteria that have annihilated tens of thousands people. However, before long, penicillin-resistant *Staphylococcus aureus* had been found and antibiotics could not be the final solution any more. After penicillin-resistant *Staphylococcus aureus* was found, methicillin was developed in 1960s, giving a new hope. But, again, MRSA (methicillin-resistant *Staphylococcus aureus*) was found in 1970s. So, since the first generation antibiotic, penicillin, was developed, reliable antibiotics having a satisfactory effect have not been developed because of resistance matter even if various attempts have been made to develop diverse antibiotics. And novel effective antibiotics are still being searched. Mankind developed vancomycin, the super-strong antibiotic, to cope with MRSA. However, VISA (vancomycin-intermediate *Staphylococcus aureus*) was found in Japan in 1997 and in Korea in 1998. And soon VRSA (vancomycin-resistant *Staphylococcus aureus*) was found in USA in 2002, which was a big issue then world widely. Even if antibiotics are still being used for the treatment of bacterial infectious disease, over-use or mis-use of antibiotics caused another problem of the generation of antibiotic resistant strains. Make matter worse, so called super-bacteria or super-bug which are resistant bacteria that nullify the treatment effect of the conventional antibiotics appeared, which is a serious social problem. Therefore, it is an urgent request to develop novel antibiotics that can treat infectious disease even caused by those bacteria having resistance against the conventional antibiotics.

The major reason of the increase of antibiotic resistant strains is antibiotic contamination of the environment including human, cattle, wild animals, cultured fishes, soil, river, and sea resulted from mis-use and over-use of antibiotics. Over-use of antibiotics is one reason for making resistance acquiring time in bacteria against newly developed antibiotics shorter than ever. But, fundamentally, most of new antibiotics have been based on the same basic structure as the conventional antibiotics and only a little modification in chemical structure has been made because of limitation in techniques. All the antibiotics on the market are facing resistance problem, and thus it is strongly required to develop a novel class antibiotic free from resistance problem of the conventional antibiotics. Novel class antibiotics developed for the last 50 years are only three, which are oxazoldinones, cyclic lipopeptides and platensimycin. It is thus still required to develop a novel class antibiotic and the novel class antibiotic is supposed to have antimicrobial activity to those bacteria having resistance against the conventional antibiotics.

Under the situation that the problem of the conventional antibiotics represented by mis- and over-use of antibiotics is international issue, bacteriophage and bacteriophage-originated lysin protein are drawing our attention as alternative antibiotics to solve the said problem. Bacteriophage and lysin protein are completely different from the conventional antibiotics class, which means they have completely different antibacterial mode of action. Therefore, it is expected that they can reduce side effects of the conventional antibiotics.

Bacteriophage is one of virus-like microorganisms infecting bacteria and generally called 'phage' in short. Bacteriophage is an organism having a simple structure wherein a central genetic material composed of nucleic acid is covered by a protein envelope. The nucleic acid is single stranded or double stranded DNA or RNA. To survive, bacteriophage needs a host bacterium and every bacterium has a specific partner bacteriophage. Bacteriophage destroys cell wall by attacking the peptidoglycan layer of cell wall. Bacteriophage was first found by Twort, an English bacteriologist. And in 1917, a French bacteriologist d'Herelle identified bacteriophage independently. The term bacteriophage means 'eating bacteria'. Owing to antibacterial activity, bacteriophage has been used for the treatment of disease in human and animal right after it was identified. Since penicillin was found by Flemming, various antibiotics have been developed and distributed. So, bacteriophage became out of interest in Western countries. However, Russia and some East European countries including Germany have constantly studied bacteriophage and some of related products have been commercialized. In 2000s, antibiotic-resistant strains became recognized as a serious problem, and therefore Western countries began to be interested in bacteriophage. It was not until 7-8 years since then that cases of industrialization of bacteriophage have been reported. That is, bacteriophage became newly recognized world-widely in the early 2000, and it has been 7-8 years that industrialization of bacteriophage was attempted. But, it is still a novel field and is being actively advanced with the development of bioengineering techniques.

The most peculiar characteristic of bacteriophage is that bacteriophage infects pathogenic bacteria and then destroys cell wall of the bacteria to kill the bacteria at last. The cell killing mechanism by bacteriophage is completely different from the conventional synthetic antibiotic mechanism which is mainly to interrupt bacterial cell wall synthesis. So, bacteriophage can demonstrate antimicrobial activity regardless of sensitivity to the conventional synthetic antibiotics. That is, it shows antibacterial effect on such multi-drug resistant strains. Bacteriophage has a specific and unique antibacterial activity against bacteria. That is, it does not affect eukaryotic cells composing human and animals.

With the advance of bioengineering techniques, studies have been actively undergoing to treat infectious organisms using bacteriophage-originated lysin protein, known to play a key role in cell-destruction by bacteriophage. A report was published in Nature in 2002 saying that lysin protein could treat *Bacillus anthracis* effectively. Since then, bacteriophage-originated lysin protein became on the spotlight. Lysin protein also has completely different antibacterial mode of action, precisely lysin protein demonstrates its antibacterial activity by directly destroying bacterial cell wall, unlike the conventional antibiotics. Attempts to use lysin protein were rather made later than attempts to use bacteriophage itself. But studies on lysin protein having high potential as a treatment agent for infectious organism related disease have been actively undergoing.

TECHNICAL PROBLEM

It is an object of the present invention to provide a bacteriophage-originated lysin protein that does not affect eukaryotic cells but have ability to kill selectively pathogenic bacteria and also have broad antibacterial activity, and a method for preventing and treating infectious disease caused by bacteria with the same.

In other words, it is an object of the present invention to provide a novel lysin protein capable of killing specifically bacteria causing infectious disease in human and animals.

It is another object of the present invention to provide a pharmaceutical composition for the prevention and treatment of bacterial infectious disease comprising the said lysin protein as an active ingredient.

TECHNICAL SOLUTION

In a preferred embodiment of the present invention, the invention provides a lysin protein having bacteria specific antimicrobial activity which comprises the amino acid sequence represented by SEQ. ID. NO: 2 and is originated from bacteriophage EFA-1 previously isolated by the present inventors.

The present inventors were well aware that the reported lysin proteins originated from bacteriophage are limited in their antimicrobial activity to a narrow spectrum of bacteria, which makes commercialization of the lysin proteins difficult. Therefore, the present inventors tried to screen a novel lysin protein having broad antimicrobial activity to overcome the said problem.

The present inventors analyzed genomes of diverse bacteriophages previously isolated by the inventors to obtain the whole genetic information of bacteriophage. And genetic information of lysin protein of each bacteriophage was obtained by comparing it with the collected sequence records of bacteriophage genomes. The present inventors completed this invention by producing recombinant protein of each lysin protein using genetic engineering technique and bioengineering technique based on the obtained genetic information of each lysin protein, followed by investigation of antimicrobial activity spectrum of the produced lysin protein and thus by selecting a lysin protein having antimicrobial activity against diverse bacteria.

The mother bacteriophage from which the lysin protein of the present invention is derived is bacteriophage EFA-1 isolated by the present inventors, which was deposited at Korean Collection for Type Cultures, Korea Research Institute of Bioscience and Biotechnology on Feb. 26, 2008 (Accession No: KCTC 11289BP). The related matters have been applied for a patent (Korean Patent Application No. 10-2008-0029847).

The present inventors obtained gene sequence encoding a lysin protein from bacteriophage EFA-1, based on which the recombinant lysin protein was produced by using genetic engineering technique and bioengineering technique. The present inventors confirmed that the produced recombinant lysin protein had antimicrobial activity against diverse bacteria.

Target bacteria of the lysin protein of the present invention are all the Gram negative and Gram positive bacteria. In a preferred embodiment of the present invention, the lysin protein of the present invention demonstrated antimicrobial activity against *Enterococcus, Streptococcus, Pseudomonas, Salmonella, Escherichia coli, Staphylococcus, Lactococcus*, and *Lactobacillus* (see Example 2, Table 1), but these are only examples and all the antimicrobial activity to broad range of bacteria cannot be described herein simply because of physical limitation. So, the lysin protein of the present invention can be effective not only in the said bacteria but also in *Enterobacteriaceae, Staphylococcus, Enterococcus, Streptococcus, Pseudomonas, Klebsiella, Escherichia coli, Providencia, Proteus, Morganella, Acinetobacter, Burkholderia, Stenotrophomonas, Alcaligenes, Mycobacterium*, etc, but not always limited thereto.

The said lysin protein has the amino acid sequence represented by SEQ. ID. NO: 2 and the gene encoding the protein has the nucleotide sequence represented by SEQ. ID. NO: 1.

In a preferred embodiment of the present invention, the present invention provides a pharmaceutical composition comprising the lysin protein originated from bacteriophage EFA-1 as an active ingredient for the prevention and treatment of bacterial infectious disease.

The bacterial infectious disease herein is exemplified by dysentery, meningitis, vaginosis, pneumonia, enteritis, prostatitis, conjunctivitis, intestinal infections, dermatitis, anthrax, brucellosis, cholerae, Salmonellosis, blackquarter, botulism, colibacillosis, contagious skin necrosis, corynebacteriosis, cystitis, endometritis, endotoxemia, enterotoxemia, glanders, leptospirosis, listeriosis, lymphadenitis, mastitis, melioidosis, paratuberculosis, pasteurellosis, plague, Q-fever, strangles, tetanus, tuberculosis, colitis, hemorrhagic septicemia, labyrinthitis, septicemia, and food poisoning, etc, but not always limited thereto and any infectious disease caused by bacteria is included as a target disease of the present invention.

The pharmaceutical composition for the prevention and treatment of bacterial infectious disease of the present invention can additionally include a pharmaceutically acceptable carrier, which is exemplified by lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, but not always limited thereto. The pharmaceutical composition for the prevention and treatment of bacterial infectious disease of the present invention can also include a lubricant, a wetting agent, a sweetener, a flavor, an emulsifier, a suspending agent, and a preservative, in addition to the above ingredients.

The pharmaceutical composition for the prevention and treatment of bacterial infectious disease of the present invention can be applied or sprayed on the lesion, and administered orally or parenterally (for example, intravenous, intramuscular, hypodermic, local or peritoneal injection).

The effective dosage of the pharmaceutical composition for the prevention and treatment of bacterial infectious disease of the present invention varies from the formulation, administration pathway, age, weight, gender, severity of a disease, diet, administration frequency and pathway, excretion and sensitivity. In general, the dosage can be determined by an experienced doctor with consideration of the goal of the treatment or preventive effect. In this invention, the pharmaceutical composition contains the lysin protein of the present invention at the concentration of 0.0001-10% (w/v), preferably 0.001-1% (w/v), and more preferably 0.1% (w/v).

The effective dosage of the pharmaceutical composition for the prevention and treatment of bacterial infectious disease of the present invention can be formulated as a unit dose medicine or as a medicine in multidose vehicle by mixing with a pharmaceutically acceptable carrier and/or excipient by the method well known to those in the art. The pharmaceutical formulation can be selected from a group consisting of ointments, solutions, suspensions or emulsions, extracts, powders, granules, tablets or capsules and additionally includes a dispersing agent or a stabilizing agent.

ADVANTAGEOUS EFFECT

The present invention provides a novel lysin protein capable of killing activity specific to various pathogenic bacteria. The lysin protein of the present invention originated from bacteriophage EFA-1 can be used as a preventive and therapeutic agent for bacterial infectious disease. The lysin protein originated from bacteriophage EFA-1 of the present invention has higher specificity to bacteria than the conventional antibiotics. That is, the lysin protein kills bacteria only and has no harm to eukaryotic cells composing human and animal. So, the lysin protein of the present invention is highly valuable as a pharmaceutical composition for the prevention and treatment of bacterial infectious disease with significantly reduced toxicity and side effects. Besides, the lysin protein of the present invention has another advantage of a broad antibacterial spectrum, unlike the reported lysin proteins showing a narrow antibacterial activity range. This is a great merit and novel characteristics which provides a great possibility for further industrial use. The lysin protein of the present invention is in completely different class from the conventional antibiotics, so that the antibacterial mechanism is also different from that of the conventional antibiotic. So, the lysin protein is even effective in the treatment of bacterial infectious disease caused by resistant bacteria against conventional antibiotics. The lysin protein of the present invention is a protein, so it is going to be decomposed in vivo or released out of body after a while, indicating that it is free from the problem of bio-concentration. Besides, when it is released to the nature, it becomes decomposed easily, suggesting that it does not cause any problem by accumulation in the nature, unlike the conventional antibiotics.

DESCRIPTION OF DRAWINGS

The application of the preferred embodiments of the present invention is best understood with reference to the accompanying drawings, wherein.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Bacteriophage and Lysin Protein

The present inventors obtained gene sequence encoding the lysin protein of the present invention from genetic information of the whole bacteriophage genome specifically infecting *Enterococcus faecalis* which was isolated previously by the present inventors and based on that the inventors produced the recombinant lysin protein using genetic engineering and bioengineering techniques. The preparation processes are described in detail hereinafter.

The present inventors extracted genome of bacteriophage EFA-1, the bacteriophage isolated and deposited at Korean Collection for Type Cultures, Korea Research Institute of Bioscience and Biotechnology on Feb. 26, 2008 (Accession No: KCTC 11289BP) by the present inventors, and the extracted genome was used for genome sequencing. Precisely, 20 ml of *Enterococcus faecali* suspension ($OD_{600}$: 1) and 1 ml of filtrate of bacteriophage suspension at the concentration of $1 \times 10^8$ pfu/ml were added to 1 L flask containing 200 ml of TSB (Tryptic Soy Broth) medium (casein digest, 17 g/L; soybean digest, 3 g/L; dextrose, 2.5 g/L; NaCl, 5 g/L; dipotassium phosphate, 2.5 g/L), followed by shaking-culture at 37° C. for 3-4 hours. Upon completion of the culture, lysis of *Enterococcus faecali* was confirmed. Then, the culture broth was filtered with 0.45 μm filter. Polyethylene glycol 8000 (20%, w/v) solution containing 2.5 M NaCl was added (⅙ volume of the filtrate used) thereto, which stood at 4° C. for overnight. Then, the solution was centrifuged at 8,000 rpm for 20 minutes to obtain bacteriophage precipitate. The precipitate was resuspended in 1 ml of phosphate buffer saline (PBS). Polyethylene glycol 8000 (20%, w/v) solution containing 2.5 M NaCl was added (⅙ volume of the resuspended solution) thereto, which stood at 4° C. for 1 hour. Then, the solution was centrifuged at 14,000 rpm for 10 minutes to obtain purified bacteriophage precipitate. The precipitate was resuspended in 500 μl PBS. To destroy the outer wall of bacteriophage, 100 μl of proteinase K (20 mg/ml and 500 μl of 10% (w/v) sodium dodecyl sulfate (SDS) were added thereto, followed by incubation at 65° C. for 1 hour. One hour later, 10 ml of the mixed solution comprising phenol, chloroform and isoamylalcohol at the ratio of 25:24:1 was added and well mixed. The mixture was centrifuged at 14,000 rpm for 10 minutes at 4° C., leading to phase separation. The upper aqueous phase was recovered, to which 100% (w/v) cold alcohol was added 2 times the volume, followed by extraction of pure genome.

Figure 1:
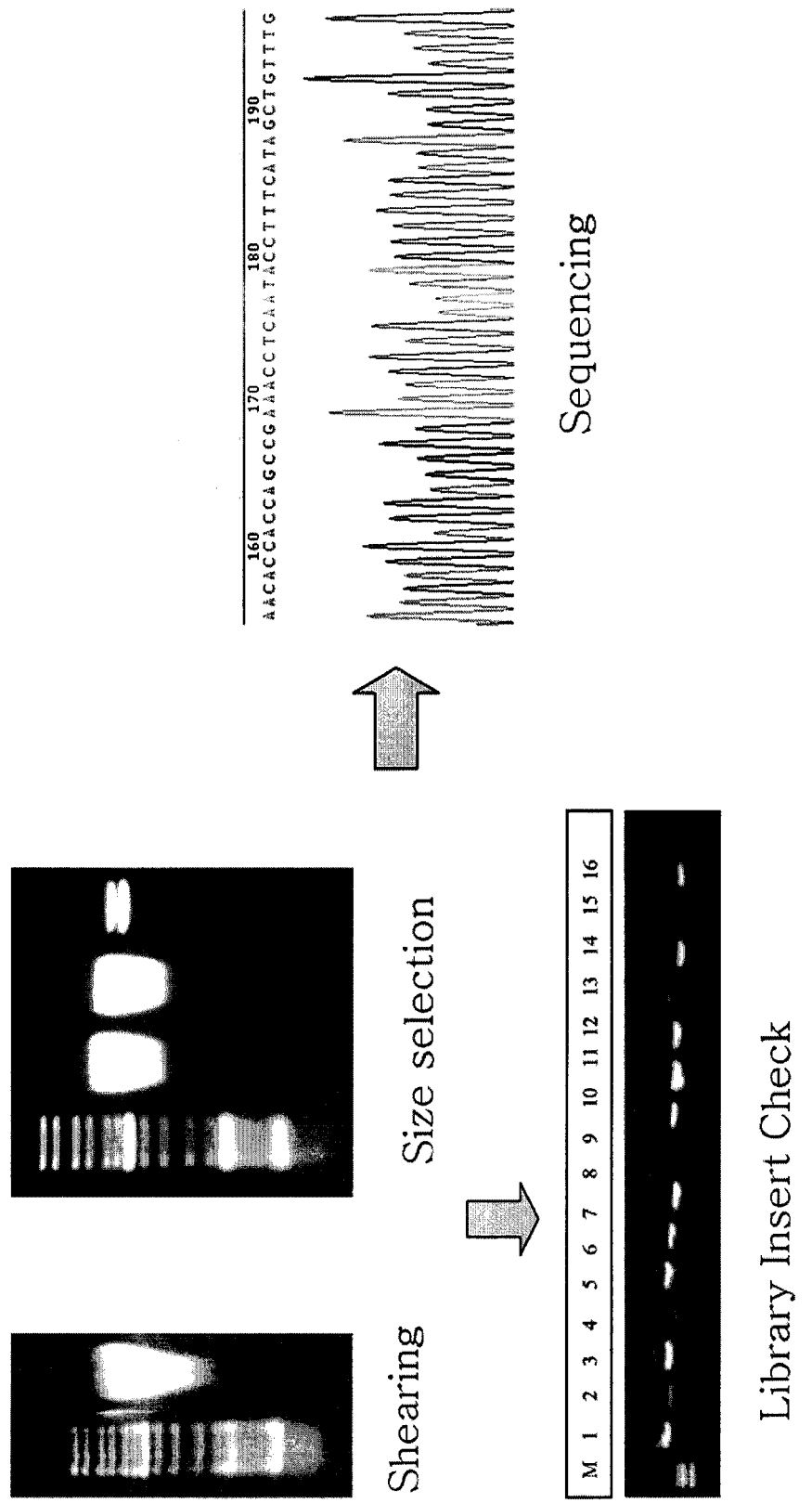
FIG. 1 is a diagram illustrating the construction procedure of the bacteriophage EFA-1 genomic DNA library.

The extracted bacteriophage genome is genomic DNA (gDNA). To sequence the gDNA, library was first constructed by shotgun library construction method which is the common method being used for gDNA library construction. More precisely, the bacteriophage genome was partially digested to 1-6 kbp fragments by random shearing using nebulizer, followed by end-repairing. Electrophoresis was performed on agarose gel to obtain gDNA fragments (inserts) of 2-5 kbp. The obtained bacteriophage gDNA fragments were ligated to pC31 vector using T4 ligase, resulting in the construction of library. E. coli DH10B' was transformed with the recombinant plasmid having the bacteriophage gDNA fragment by heat-shock transformation. The transformant having the recombinant plasmid was cultured, from which the plasmid harboring gene fragment was extracted using plasmid purification kit (iNtRON). Electrophoresis was performed with the extracted plasmids to examine whether the recombinant plasmids have the gene fragment based on its size. At last, 16 clones were finally selected. Large-scale plasmid preparation from the selected clones was performed by the conventional method, followed by nucleotide sequencing. Single contig map was made by using the result of gene sequencing and the whole genome sequence of 21,115 by was analyzed by primer walking. This procedure is illustrated in FIG. 1. The identified sequence is the total genome sequence of bacteriophage and the sequence is presented in Korean Patent Application No 10-2008-0029847.

The obtained genome sequence was compared with the collected sequence records of bacteriophage genomes using NCBI Blast (http://www.ncbi.nlm.nih.gov/BLAST/), by which gene sequence corresponding to the lysin protein was presumed. The presumed lysin protein gene sequence (987 bp) was represented by SEQ. ID. NO: 1. The amino acid sequence (328 amino acid residues) corresponding the lysin protein gene sequence was represented by SEQ. ID. NO: 2. The amino acid sequence was compared with other reported lysin protein sequences and as a result the lysin protein originated from bacteriophage EFA-1 was confirmed to be the novel lysin protein that has never been reported, yet.

Lysin protein expression plasmid was constructed to produce the lysin protein. The lysin protein gene was cloned in pBAD-TOPO vector (Invitrogen) using Nco I and Not I restriction enzyme sites by PCR cloning. Before cloning, enterokinase cleavage site of pBAD-TOPO vector was eliminated and instead Not I restriction enzyme site was inserted in that place. After cloning, site-directed mutagenesis was carried out so that translation starts at the proper start codon using a site-directed mutagenesis kit (iNtRON). As a result, the lysin protein expression plasmid was constructed and named pBAD::EFAL-1. E. coli BL21(DE3)/pLysS (Novagen) was transformed with the lysin protein expression plasmid. It was used as a lysin protein production host.

Lysin protein was produced using the production host. Over-expression induction process is described in detail hereinafter. The constructed plasmid contained ampicillin resistant gene and the production host contained chloramphenicol resistant gene. So, the lysin protein production host was inoculated in 5 ml of LB medium (tryptone, 10 g/L; yeast extract, 5 g/L; sodium chloride, 10 g/L) containing ampicillin (50 µg/ml) and chloramphenicol (50 µg/ml), followed by shaking-culture at 37° C. for overnight. 100 µl of the culture broth was re-inoculated in 10 ml of fresh LB medium containing ampicillin (50 µg/ml) and chloramphenicol (50 µg/ml), followed by shaking-culture at 37° C. When $OD_{600}$ reached 0.5, L-arabinose was added (final conc: 0.2%) to induce lysin protein expression. Shaking-culture was allowed to continue for additional 4 hours at 37° C. Upon completion of the culture, 1 ml of the culture broth was taken and centrifuged at 8,000 rpm for 5 minutes to obtain cell precipitate. 100 µl of 1% (w/v) SDS solution was added to the cell precipitate to lyse the cells. 12 µl of the cell lysate was used for electrophoresis. 3 µl of 5× sample loading buffer for electrophoresis was added to the cell lysate taken, followed by boiling for 5 minutes in water bath. Electrophoresis was performed by the conventional method to confirm over-expression of the lysin protein.

Figure 2:
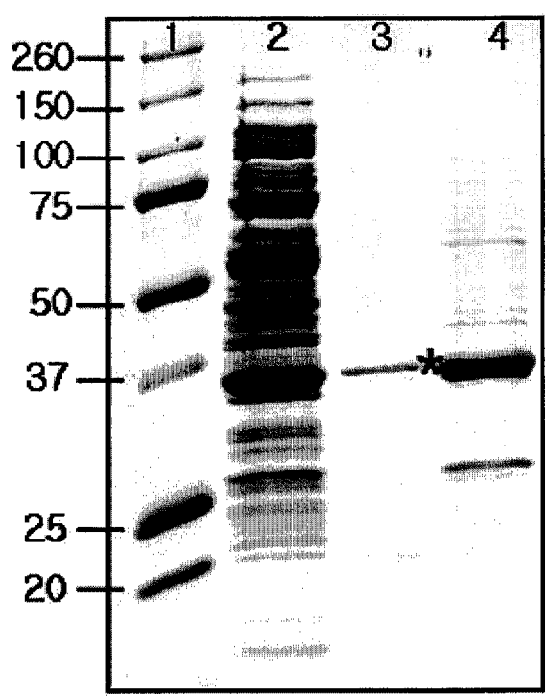
FIG. 2 is a photograph illustrating the result of electrophoresis with the purified lysin protein. Lane 1: protein size marker (unit: kDa), Lane 2: protein fraction obtained from desalting chromatography, Lane 3: protein fraction 1 obtained from ion-exchange chromatography, and Lane 4: protein fraction 2 obtained from ion-exchange chromatography. *: position of lysin protein.

After confirmation of over-expression, the large-scale production and purification were performed. 40 µl of glycerol cell stock of the lysin protein production host was inoculated in 200 ml of LB medium (tryptone, 10 g/L; yeast extract, 5 g/L; sodium chloride, 10 g/L) containing ampicillin (50 µg/ml) and chloramphenicol (50 µg/ml), followed by shaking-culture at 37° C. for overnight. 200 ml of the overnight-culture broth was re-inoculated in 2 L of fresh LB medium containing ampicillin (50 µg/ml) and chloramphenicol (50 µg/ml), followed by fermentation at 37° C. When $OD_{600}$ reached 0.5, L-arabinose was added (final conc: 0.2%) to induce lysin protein expression. Fermentation was allowed to continue for additional 4 hours at 37° C. 2 L of the culture broth was centrifuged at 8,000 rpm for 10 minutes at 4° C. to obtain cell precipitate. The cell precipitate was suspended in 40 ml of 30 mM Tris-HCl buffer (pH 8.0). The cells in the cell suspension were lysed by ultrasonication. Particularly, ultrasonication was performed as follows: ultrasonic wave was given for 10 seconds to lyse cells and stopped for 10 seconds, which was repeated for 10 minutes. The obtained whole cell lysate was centrifuged at 13,000 rpm at 4° C. for 20 minutes to remove cell debris. Polyethyleneimine (PEI) was added at the final concentration of 0.2% to the supernatant obtained from the centrifugation above, which stood at 4° C. for one hour, followed by centrifugation again at 13,000 rpm at 4° C. for 10 minutes. Ammonium sulfate was added to the supernatant at the final concentration of 15% (w/v), which stood in ice for 30 minutes. 30 minutes later, the mixture was centrifuged at 13,000 rpm at 4° C. for 30 minutes. Upon completion of centrifugation, supernatant was recovered and transferred to a new tube, followed by filtering using 0.22 µm filter. Then the filtrate was concentrated to 3 ml using Centriprep (Amicon; 10,000 MW cut-off). To eliminate ammonium sulfate included in the protein solution, desalting chromatography was performed. At this time, superdex G-75 (15 mm×30 cm) was used as a column resin and 30 mM Tris-HCl buffer (pH 8.0) was used as a buffer. Anion-exchange chromatography was performed with the protein fractions obtained by desalting chromatography. At this time, Mono Q (GE Healthcare; 5 mm×50 mm) was used as an anion-exchange resin. Before chromatography, chromatography column was equilibrated using adsorption buffer (30 mM Tris-HCl, pH. 8.0). After loading lysin protein solution on the column, washing was performed using 10 ml of adsorption buffer. Endogenous proteins of the E. coli host were not absorbed on the column resin and washed out. The lysin protein was eluted by using elution buffer (25 mM Tris-HCl, pH 8.0) containing potassium chloride at different concentrations from 0 to 1 M. To remove potassium chloride used for the elution of the lysin protein, the eluent fraction containing lysin protein was dialyzed against 30 mM of Tris-HCl buffer (pH 8.0) at 4° C. for overnight. The dialysate was concentrated through performing dialysis of protein solution against dried polyethyleneglycol 20,000. The result is shown in FIG. 2.

Example 2

Antibacterial Activity of Lysin Protein to Diverse Bacteria

The present inventors investigated antibacterial activity of the lysin protein of the present invention originated from bacteriophage EFA-1 to various bacteria. The bacteria used in this investigation were distributed from CCARM (Culture Collection of Antimicrobial Resistant Microbes; Seoul Women's University, Seoul 139-774, Korea) or ATCC (The American Type Culture Collection, USA), or isolated by the present inventors.

Figure 3:
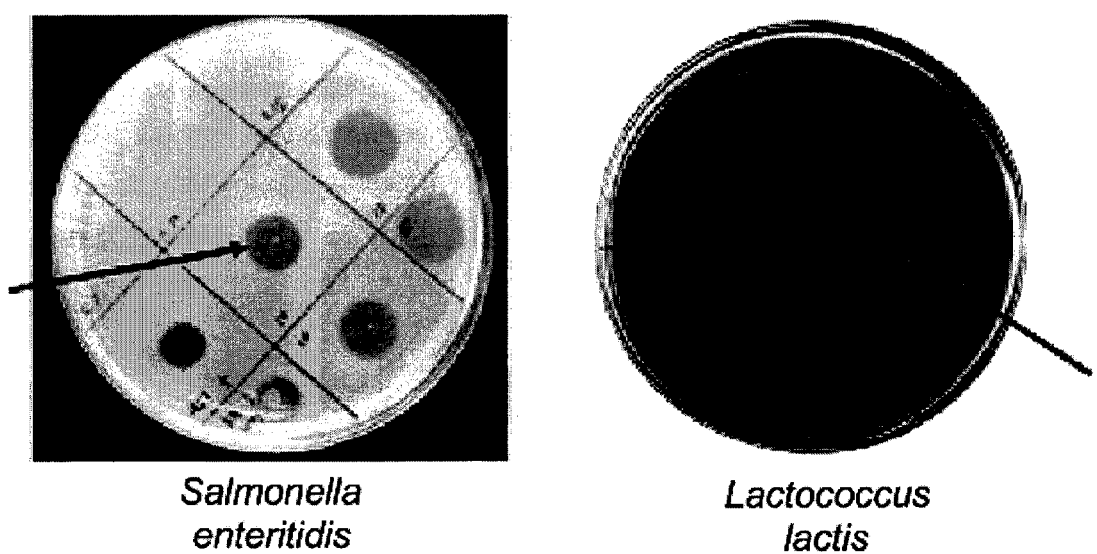
FIG. 3 is a set of photographs illustrating an example of antibacterial activity shown in Table 1, in which transparent clear zone marked by arrow was generated by the antibacterial activity of the lysin protein of the present invention. Left: Gram-negative *Salmonella enteritidis*, Right: Gram-positive *Lactococcus lactis*. Almost the same clear zones were formed in other bacteria.

1 ml of each bacteria culture broth ($OD_{600}$: 1) was spread on TSA (Tryptic Soy Agar) plate medium (casein digest, 15 g/L; soybean digest, 5 g/L; NaCl, 5 g/L; agar, 15 g/L) or general LB agar plate medium, followed by drying. The protein solution containing lysin protein prepared in Example 1 was dropped on the each plate prepared as described above (10 μg of the lysin per test). The plates were cultured in a 37° C. incubator for 30 minutes and bacteria lysis was examined. The results are as follows and the representative photographs are shown in FIG. 3.

TABLE 1

| Species name | Strain information[1] | Bacteriolytic activity[2] |
|---|---|---|
| Enterococcus faecalis | 5168(CCARM) | ++ |
| Enterococcus faecalis | 5169(CCARM) | ++ |
| Enterococcus faecalis | 5170(CCARM) | ++ |
| Enterococcus faecalis | 5171(CCARM) | ++ |
| Enterococcus faecalis | 5172(CCARM) | + |
| Enterococcus faecalis | 5173(CCARM) | + |
| Enterococcus faecalis | 5174(CCARM) | + |
| Enterococcus faecalis | 5175(CCARM) | + |
| Enterococcus faecalis | 5176(CCARM) | + |
| Enterococcus faecalis | 5177(CCARM) | + |
| Enterococcus faecalis | 0011(ATCC) | + |
| Enterococcus faecium | 5192(CCARM) | ++ |
| Enterococcus faecium | 5193(CCARM) | ++ |
| Enterococcus faecium | 5195(CCARM) | ++ |
| Enterococcus faecium | 5196(CCARM) | ++ |
| Enterococcus faecium | 5197(CCARM) | ++ |
| Enterococcus faecium | 5198(CCARM) | ++ |
| Enterococcus faecium | 5199(CCARM) | ++ |
| Escherichia coli | isolate | + |
| Lactococcus lactis | isolate | ++ |
| Lactobacillus plantarum | isolate | ++ |
| Pseudomonas aeruginosa | Isolate | ++ |
| Salmonella enteritidis | Isolate | + |
| Salmonella gallinarum | Isolate | + |
| Staphylococcus aureus | isolate | + |
| Streptococcus agalactiae | 7077 (ATCC) | + |
| Streptococcus mutans | CCARM 0079 | ++ |
| Streptococcus mitis | CCARM 0143 | + |
| Streptococcus uberis | isolate | ++ |

[1]Strain information: CCARM, Culture Collection of Antimicrobial Resistant Microbes; ATCC, The American Type Culture Collection
[2]Bacteriolytic activity: ++, strong bacteriolytic activity; +, moderate bacteriolytic activity (investigated 30 minutes after the treatment).
Strong bacteriolytic activity and moderate bacteriolytic activity were comparative values. The two cases must have bacteriolytic activity As a result, the lysin protein of the present invention had antibacterial activity to not only Gram negative bacteria such as *Pseudomonas*, *Salmonella*, and *Escherichia coli* but also Gram positive bacteria such as *Enterococcus*, *Streptococcus*, *Staphylococcus*, *Lactococcus*, and *Lactobacillus*. So, the lysin protein of the present invention was concluded to have a broad antibacterial activity to both Gram negative and Gram positive bacteria. This result indicates that the lysin protein of the present invention had a broad antibacterial spectrum unlike the reported lysin protein having a narrow antibacterial activity and limited specificity. The lysin protein of the present invention is a novel protein having different characteristics from the conventional one, suggesting potential for industrialization.

Therefore, the lysin protein of the present invention can be effectively used for the prevention and treatment of infectious disease caused by various bacteria.

Example 3

Cytotoxicity Test in Eukaryotic Cells

MTT assay was performed to investigate cytotoxicity of lysin protein of the present invention to animal cells, one of eukaryotic cells. Animal cells do not have cell walls but have cell membranes, which is the characteristics of eukaryotic cells. MTT assay is the method of analyzing cell viability based on the principle that yellow water-soluble tetrazolium is reduced into violet insoluble formazan by dehydrogenase in active mitochondria of viable cell. So, it is a method to count viable cell number by measuring optical density of formazan. The cell lines used in this example were HeLa cell line, one of human cell lines, and Raw cell line originated from rat, one of animal cell lines. Particularly, each cell line was cultured in RPMI 1640 supplemented with 10% Fetal bovine serum (FBS) and gentamycin for 3-4 days. The cells were harvested, followed by counting cell number/ml using hemocytometer. The cells were distributed in each well of a 96-well micro plate at the concentration of $1 \times 10^4$ cells/20 μl diluted in RPMI1640. Each well was treated as shown in Table 2.

TABLE 2

| | Well 1 | Well 2 | Well 3 | Well 4 | Well 5 |
|---|---|---|---|---|---|
| Medium | 200 μl | 200 μl | 180 μl | 180 μl | 180 μl |
| Cell | — | — | $1 \times 10^4$ cells/20 μl | $1 \times 10^4$ cells/20 μl | $1 \times 10^4$ cells/20 μl |
| PBS | 3 μl | — | 3 μl | 2.7 μl | — |
| Lysin protein solution | — | 3 μl | — | 0.3 μl | 3 μl |
| Total Reaction volume | 203 μl | 203 μl | 203 μl | 203 μl | 203 μl |
| Comment | | | | Containing 10 μg of lysin protein | Containing 100 μg of lysin protein |

The 96-well micro plate was incubated in a 37° C. $CO_2$ incubator for 72 hours. 72 hours later, 10 μl of MTT solution (5 mg/ml) was added to each well, followed by further incubation in a $CO_2$ incubator for 3 hours. 3 hours later, 100 μl of isopropyl alcohol containing 0.04 M HCl was added to each well to terminate the incubation. Upon completion of the incubation, 50 μl of dimethyl sulfoxide (DMSO) was added to each well, followed by solubilization of insoluble colored materials by pipetting. Each sample was diluted with water to ⅕ and $OD_{570}$ was measured. The value of $OD_{570}$ is proportional to viable cell number and the results are as follows. The presented values are the average value of the results of three times repeated experiments. Standard deviation is not presented because deviations between the experiments were not significant.

TABLE 3

| | Well 1 | Well 2 | Well 3 | Well 4 | Well 5 |
|---|---|---|---|---|---|
| Hela cell | 0.0 | −0.0046 | 1.4649 | 1.3417 | 1.5335 |
| Raw cell | 0.0 | −0.0012 | 1.5827 | 1.7821 | 1.7972 |

The result of well #3, the negative control not treated with lysin protein, was compared with those of well #4 and well #5, experimental groups treated with lysin protein of the present invention. And the results were not much different, suggesting that cell number of each well is similar. So, the lysin protein of the present invention was confirmed to have antibacterial activity to bacteria but not have cytotoxicity to eukaryotic cells including animal cells. The lysin protein was excessively applied in every experiment but no cytotoxicity was observed. Therefore, it is anticipated that the lysin protein of the present invention has bacteria specific antimicrobial activity and is very safe in use for animals including human because it has no cytotoxicity to eukaryotic cells.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

---

The invention claimed:

1. An isolated or recombinant lysin protein comprising the amino acid sequence of SEQ. ID. NO: 2.

2. The lysin protein according to claim 1, wherein the lysin protein is originated from bacteriophage EFA-1, deposited as Accession No: KCTC 11289BP).

3. A pharmaceutical composition comprising the lysin protein of claim 1.

4. A method of killing bacteria comprising contacting the bacteria with the lysin protein of claim 1.

5. The method of claim 4, wherein the bacteria are gram positive.

6. The method of claim 5, wherein the gram positive bacteria are Staphylococcus, Streptococcus, Enterococcus, Lactococcus, or Lactobacillus.

7. A method of treating an infectious bacterial disease in a subject comprising administering to the subject the pharmaceutical composition of claim 3.

8. The method of claim 7, wherein the bacterial disease is an infection with gram positive or gram negative bacteria.

9. The method of claim 8, wherein the gram negative bacteria is Pseudomonas, Salmonella, or Escherichia coli.

10. The method of claim 8, wherein the gram positive bacteria is Staphylococcus, Streptococcus, Enterococcus, Lactococcus, or Lactobacillus.

11. The method of claim 4, wherein the bacteria are gram negative and gram positive bacteria.

12. The method of claim 11, wherein the gram negative bacteria are Pseudomonas, Salmonella, or Escherichia coli, and the gram positive bacteria are Staphylococcus, Streptococcus, Enterococcus, Lactococcus, Lactobacillus, and Mycobacterium.

* * * * *

SEQUENCE LISTING

```
<160> NUMBER OF SEQ ID NOS: 2

<210> SEQ ID NO 1
<211> LENGTH: 987
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 1
atgaaattaa aaggaatttt attatcagta gtaacaacat ttggattgct ttttggtgca      60
acaaatgtac aagcatatga agtcaacaac gaatttaatt tacaaccatg ggaaggtagc     120
caacaactgg catatcctaa taaaatcatc ttacatgaaa cagctaatcc acgtgcaaca     180
ggtcgtaatg aagctacgta tatgaaaaac aactggttta atgcacatac tacagccatt     240
gttggtgatg gtggcattgt ttataaagta gcaccagaag gtaacgtatc atggggtgct     300
ggtaatgcta acccttacgc accagttcaa attgagttac aacatacaaa cgaccctgaa     360
ctatttaaag ccaactataa agcatatgtt gactatacac gggacatggg caaaaagttt     420
ggtattccaa tgacacttga ccaaggtggt tcactttggg aaaaaggtgt agtatctcac     480
caatgggtta cagactttgt atggggtgac cacacagacc cttatggtta cttagctaag     540
atgggtatca gtaaagctca attggcacat gacttagcta atggggttag tggtaacaca     600
gcaacaccta ctcctaaacc tgataaacct aagccaacac aacctagtaa acctagtaat     660
aaaaaacgct tcaattaccg tgtagatggc ttagagtatg taaatggaat gtggcaaatc     720
tacaacgaac atttaggtaa aattgacttt aattggactt aaaacggtat tccagtagaa     780
gttgttgaca aggttaatcc agcaacagga caacctacta aggaccaagt actaaaagtt     840
ggcgactatt tcaacttcca agaaaacagc acaggtgtag tacaagagca aacaccttac     900
atgggttata cattatctca tgtacaatta ccaaatgaat ttatctggtt gttcacagat     960
agtaaacaag ccttaatgta tcaataa                                         987

<210> SEQ ID NO 2
<211> LENGTH: 328
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 2

Met Lys Leu Lys Gly Ile Leu Leu Ser Val Val Thr Thr Phe Gly Leu
  1               5                  10                  15

Leu Phe Gly Ala Thr Asn Val Gln Ala Tyr Glu Val Asn Asn Glu Phe
             20                  25                  30

Asn Leu Gln Pro Trp Glu Gly Ser Gln Gln Leu Ala Tyr Pro Asn Lys
         35                  40                  45
```

-continued

```
Ile Ile Leu His Glu Thr Ala Asn Pro Arg Ala Thr Gly Arg Asn Glu
    50                  55                  60

Ala Thr Tyr Met Lys Asn Asn Trp Phe Asn Ala His Thr Thr Ala Ile
65                  70                  75                  80

Val Gly Asp Gly Gly Ile Val Tyr Lys Val Ala Pro Glu Gly Asn Val
                85                  90                  95

Ser Trp Gly Ala Gly Asn Ala Asn Pro Tyr Ala Pro Val Gln Ile Glu
                100                 105                 110

Leu Gln His Thr Asn Asp Pro Glu Leu Phe Lys Ala Asn Tyr Lys Ala
            115                 120                 125

Tyr Val Asp Tyr Thr Arg Asp Met Gly Lys Lys Phe Gly Ile Pro Met
        130                 135                 140

Thr Leu Asp Gln Gly Gly Ser Leu Trp Glu Lys Gly Val Val Ser His
145                 150                 155                 160

Gln Trp Val Thr Asp Phe Val Trp Gly Asp His Thr Asp Pro Tyr Gly
                165                 170                 175

Tyr Leu Ala Lys Met Gly Ile Ser Lys Ala Gln Leu Ala His Asp Leu
            180                 185                 190

Ala Asn Gly Val Ser Gly Asn Thr Ala Thr Pro Thr Pro Lys Pro Asp
        195                 200                 205

Lys Pro Lys Pro Thr Gln Pro Ser Lys Pro Ser Asn Lys Lys Arg Phe
    210                 215                 220

Asn Tyr Arg Val Asp Gly Leu Glu Tyr Val Asn Gly Met Trp Gln Ile
225                 230                 235                 240

Tyr Asn Glu His Leu Gly Lys Ile Asp Phe Asn Trp Thr Glu Asn Gly
                245                 250                 255

Ile Pro Val Glu Val Val Asp Lys Val Asn Pro Ala Thr Gly Gln Pro
                260                 265                 270

Thr Lys Asp Gln Val Leu Lys Val Gly Asp Tyr Phe Asn Phe Gln Glu
            275                 280                 285

Asn Ser Thr Gly Val Val Gln Glu Gln Thr Pro Tyr Met Gly Tyr Thr
    290                 295                 300

Leu Ser His Val Gln Leu Pro Asn Glu Phe Ile Trp Leu Phe Thr Asp
305                 310                 315                 320

Ser Lys Gln Ala Leu Met Tyr Gln
                325
```